United States Patent [19]

Atteberry et al.

[11] Patent Number: 5,502,378
[45] Date of Patent: Mar. 26, 1996

[54] FLUID PARTICLE SENSOR INCLUDING A CONTAINER, A FIRST COIL AND A SECOND COIL DISPOSED ABOUT A MAGNET LOCATED ADJACENT THE CONTAINER FOR ATTRACTING THE PARTICLES

[75] Inventors: Lonnie D. Atteberry, Peoria Hts.; Timothy A. Boston, Tremont; John W. Crayton, Washington; Jeffrey J. Riebschlager, Toluca; Noel J. Rytter, Peoria, all of Ill.

[73] Assignee: Caterpillar, Peoria, Ill.

[21] Appl. No.: 338,724

[22] Filed: Nov. 14, 1994

Related U.S. Application Data

[63] Continuation-in-part of Ser. No. 95,559, Jul. 26, 1993, abandoned.

[51] Int. Cl.[6] .......................... G01N 27/74; G08B 17/12
[52] U.S. Cl. .............................................. 324/204; 340/631
[58] Field of Search ............................ 364/579; 324/204, 324/236, 225, 207.12; 73/861.08, 861.11, 861.13, 10, 53.05; 340/631

[56] References Cited

U.S. PATENT DOCUMENTS

| | | | |
|---|---|---|---|
| 4,195,260 | 3/1980 | Sakamoto | 324/204 |
| 5,118,410 | 6/1992 | Rumberger | 324/204 |
| 5,179,346 | 1/1993 | McGee et al. | 324/204 |

FOREIGN PATENT DOCUMENTS

| | | | |
|---|---|---|---|
| 2132358 | 7/1984 | United Kingdom | 324/204 |

*Primary Examiner*—Sandra L. O'Shea
*Assistant Examiner*—Roger C. Phillips
*Attorney, Agent, or Firm*—David M. Masterson

[57] ABSTRACT

In one aspect of the present invention, a sensor detects particles within a fluid. The sensor includes a housing that defines a cavity. A magnet is disposed adjacent the cavity bottom to attract particles into the cavity. A first coil is wound about the outer surface of the cavity. The induction of the first coil is responsive to the particle accumulation within the cavity. A second coil is wound about the magnet. The induction of the second coil is responsive to the temperature of the fluid and independent to the particle accumulation within the cavity.

21 Claims, 5 Drawing Sheets

FLUID PARTICLE SENSOR INCLUDING A CONTAINER, A FIRST COIL AND A SECOND COIL DISPOSED ABOUT A MAGNET LOCATED ADJACENT THE CONTAINER FOR ATTRACTING THE PARTICLES

This is a Continuation-in-Part of application Ser. No. 08/095,559, filed on Jul. 26, 1993, now abandoned.

TECHNICAL FIELD

This invention relates generally to an apparatus for detecting electrically inductive particles in a fluid medium and more particularly for detecting the presence of ferrous metal particles in a lubricant.

BACKGROUND ART

Mechanical systems (engines, transmissions) utilize a lubricant (oil) to dissipate heat within the system and to reduce wear on system components. However, due to the nature of the systems, wear does occur, resulting in the presence of small metallic flakes or particles in the oil.

Due to the normal wear and to the natural breakdown of the oil, the oil in such systems must be changed periodically. This is typically done on a time or usage basis, for example, every 90 days or 2000 hours of use. While small metal particles may result from normal wear, larger particles are usually an indication of abnormal wear or a more serious problem. For example, if the gears within a transmission are not meshing properly, the resulting wear creates abnormal amounts of metal particles within the lubricant. Under normal maintenance procedures, the metal particles would be present in the lubricant for an extended period of time. If this condition is not identified and the appropriate repairs completed more expensive repairs, including the replacement of major system components, may result.

The present invention is directed to overcoming one or more of the problems as set forth above.

DISCLOSURE OF THE INVENTION

In one aspect of the present invention, a sensor detects particles within a fluid. The sensor includes a housing that defines a cavity. A magnet is disposed adjacent the cavity bottom to attract particles into the cavity. A first coil is wound about the outer surface of the cavity. The induction of the first coil is responsive to the particle accumulation within the cavity. A second coil is wound about the magnet. The induction of the second coil is responsive to the temperature of the fluid and independent to the particle accumulation within the cavity.

BRIEF DESCRIPTION OF THE DRAWINGS

For a better understanding of the present invention, reference may be made to the accompanying drawings in which.

BEST MODE FOR CARRYING OUT THE INVENTION

Figure 1:
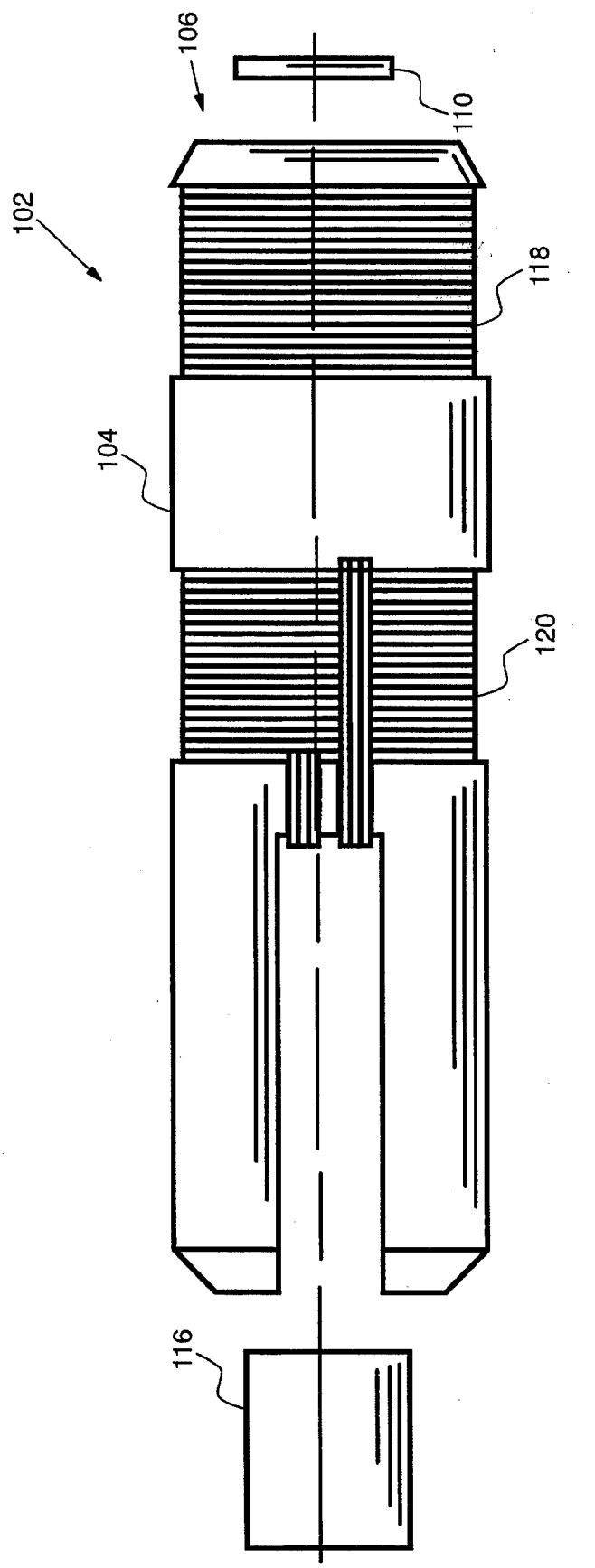
FIG. 1 is an exploded view of a housing that includes a cavity, coil, and magnet arrangement of an apparatus for detecting particles within a fluid, according to an embodiment of the present invention.
Figure 2:
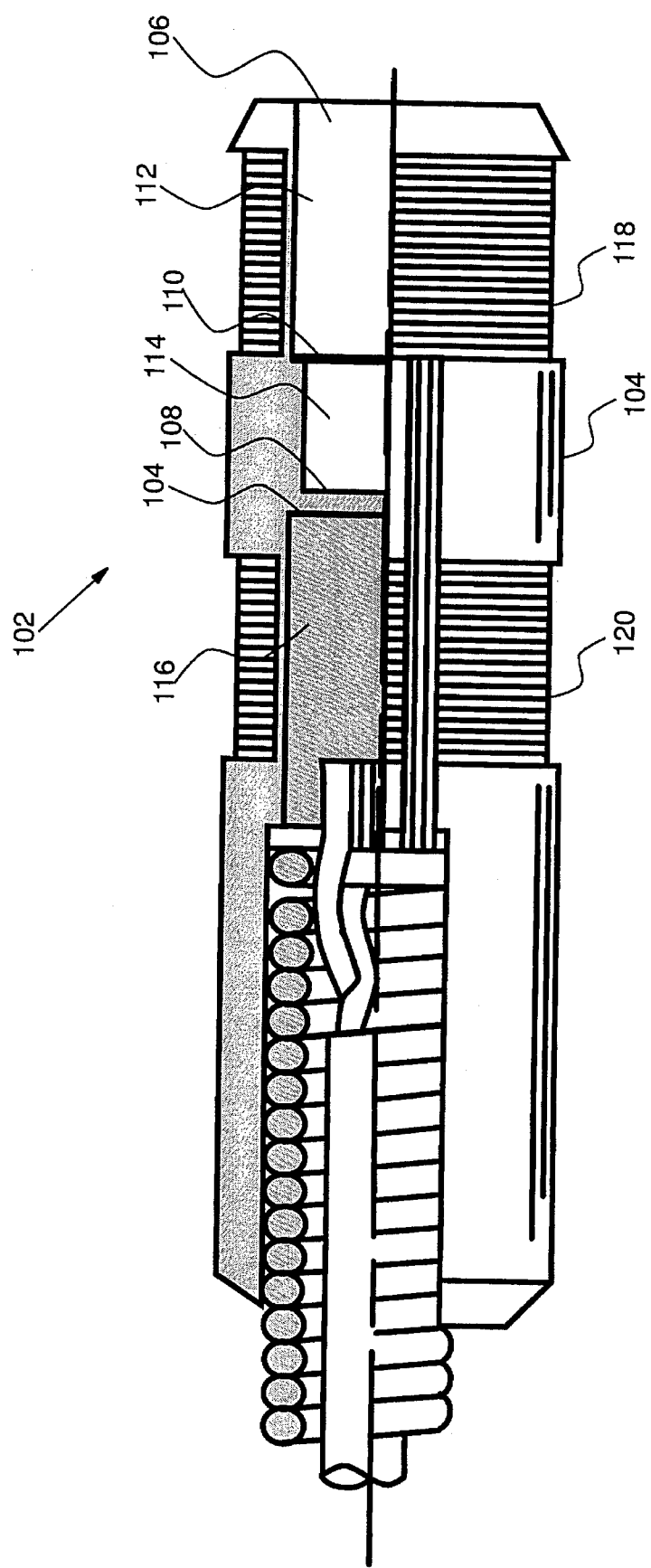
FIG. 2 is a partial, cutaway view of the particle detecting apparatus.

With reference to FIGS. 1 and 2, the present invention 102 is adapted to detect particles within the transmission fluid of a final drive and is hereafter referred to as apparatus or particle sensor. It should be noted however, that the use of the present invention for a final drive is for discussion purposes only and is not limited to such. The present invention may be adapted, for example, for use in engine oil pans, transmissions, differentials, torque converters, hydraulic systems, and other similar systems.

The particle sensor 102 includes a housing 104 preferably made of plastic. The housing 104 forms a cavity 106 which has a bottom surface 108. The cavity 106 is used for capturing and holding particles within the oil. A screen 110 is disposed in the cavity 106, which divides the cavity into an upper portion 112 and a lower portion 114. Advantageously, the screen 110 passes smaller particles to the lower portion 114 while it retains larger particles in the upper portion 112. Preferably, the screen 504 is constructed from a nonmagnetic material, e.g., polyester. The type and size of the screen and therefore the relative size of "large" and "small" particles is dependent upon the working environment. The screen 110 may be bonded to the housing 104.

A magnet 116 is disposed adjacent the bottom surface 108 of the cavity 106. The magnet 116 attracts and contains the particles within the cavity 106. A first coil 118 is wound in the form of a helix about the proximity of the cavity 106. Accordingly, the induction of the first coil 118 is responsive to the particles that are accumulated within the cavity 106. More particularly, the inductance of the first coil is responsive to the accumulated amount of particles within the upper cavity portion 112, and independent to the accumulated amount of particles within the lower cavity portion 114.

Though the inductance of the first coil 118 is relatively constant in the absence of accumulated particles, the inductance can change due to changes in the temperature of the fluid. Advantageously, a second coil 120 is provided to compensate for the changing temperature of the fluid. The second coil 120 is arranged such that its inductance is affected only by the fluid temperature, and not to the particles accumulated within the cavity. The second coil 120 is wound in the form of a helix about the magnet 116, and is spaced apart from the first coil 118. The inductance of the second coil 120, therefore, is used as a baseline for determining the presence of particles within the cavity.

In the preferred embodiment, the first and second coils 118,120 are identical and are constructed of #38 insulated wire with 300 turns.

Figure 3:
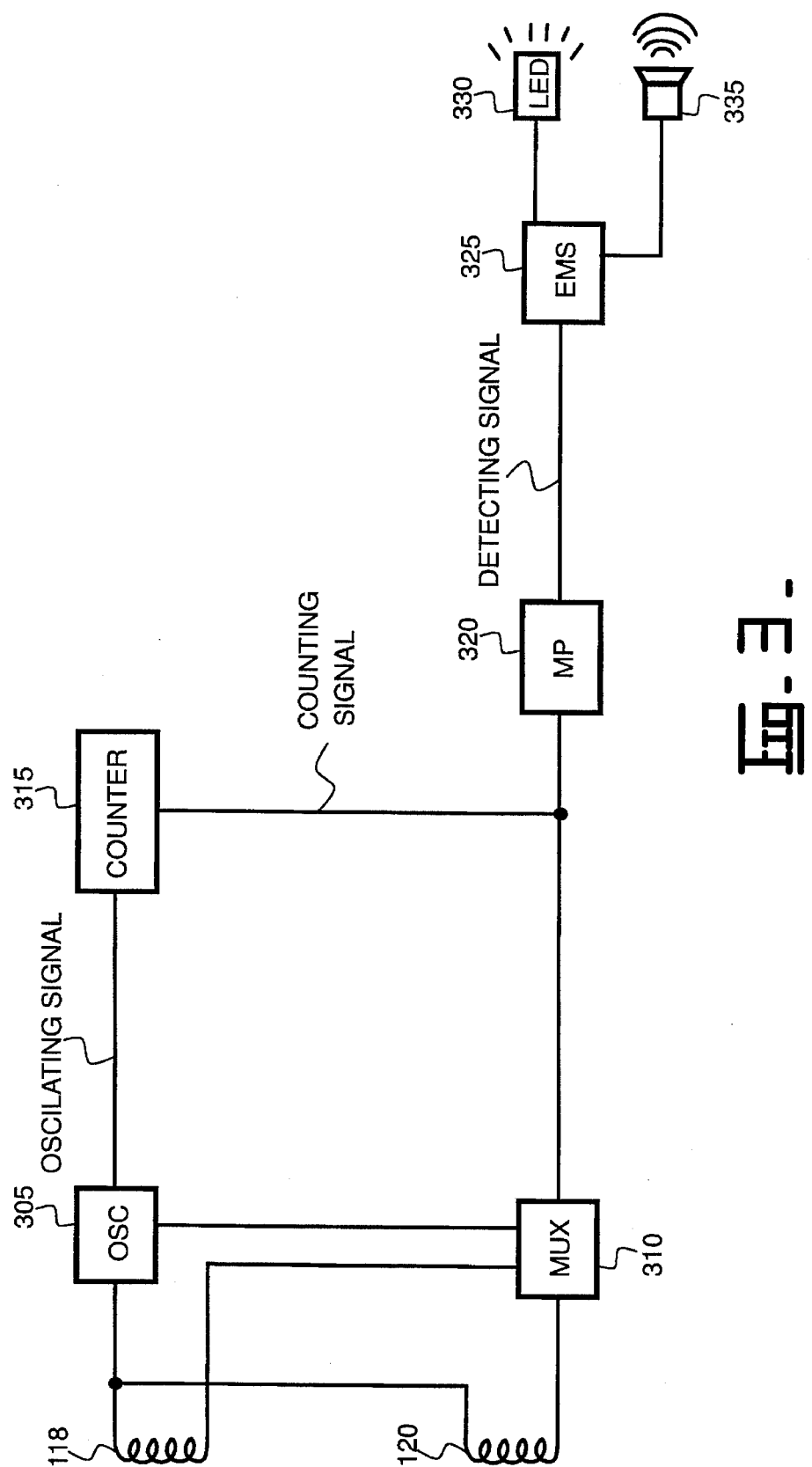
FIG. 3 is a block diagram of the electronic circuitry associated with the particle detecting apparatus.

Reference is now made to FIG. 3, which describes the electronic circuitry associated with the present invention. An oscillator 305 is provided to energize both the first and second coils 118,120. In the preferred embodiment, the oscillator consists of a 555 timer which energizes the coils with an oscillating waveform, such as a square waveform. A multiplexer 310 is provided to allow only one coil to energized at a given time. Consequently, the frequency of the oscillating waveform will be directly related to the inductance of the energized coil.

A counter 315 is provided to tally the number of pulses associated with the oscillating waveform. For example, the oscillator 305 will energize one coil, while the counter 315 tallies the number of pulses of the oscillating waveform associated with the one coil. Once the number of pulses reaches a predetermined number, then the counter resets. Responsively, the multiplexer 310 causes the other coil to begin energization. Meanwhile, the counter 315 tallies the number of pulses of the oscillating waveform associated with the other coil.

The counter 315 additionally produces a counting signal. The counting signal is a continuous pulse-width-modulated signal wherein the duration of the "high" pulse level is responsive to one coil being energized, e.g., the first coil 118, while the "low" pulse level is responsive to the other coil being energized, e.g., the second coil 120. More particularly, the "high" pulse level is responsive to the frequency of the first coil 118, which is indicative of the first coil inductance. The "low" pulse level is responsive the frequency of the second coil 120, which is indicative of the second coil inductance.

For example, when no particle accumulation exists in the upper portion of the cavity 106, the inductance of each coil 118,120 remains the same. Consequently, the oscillating waveform associated with each coil is produced with the same frequency, which causes a counting signal to be produced with a 50% duty cycle (the duration of the "high" and "low" pulse levels are the same). However, when particles begin accumulating in the upper portion of the cavity 106, the inductance associated with the first coil 118 increases proportionally, which causes the frequency of the associated oscillating signal to decrease. Resultingly, the duration of the "high" pulse level of the counting signal will increase in magnitude because it takes longer to count to the predetermined number of pulses due to the lower frequency. Thus, the duty cycle of the counting signal increases proportional to the increasing inductance associated with the first coil 118, which is indicative of large particle accumulation.

The counting signal is delivered to a microprocessor 320, which produces a detecting signal having a duty cycle that is responsive to the duty cycle of the counting signal in order to provide for greater resolution. For example, a counting signal having a duty cycle of 50% may correspond to the microprocessor producing a detecting signal having a duty cycle of 5%, which is indicative of no particle accumulation in the upper portion of the cavity 106. Meanwhile a counting signal having a duty cycle of 55% may correspond to a detecting signal having a duty cycle of 95%, which is indicative of a very large particle or a substantial amount of particle accumulation in the upper portion of the cavity 106.

As shown in FIG. 3, the microprocessor delivers the detecting signal to an electronic monitoring system 325. The electronic monitoring system 325 provides a warning signal to the vehicle operator in response to the duty cycle of the detecting signal being above a predetermined value. The electronic monitoring system 325 may include an LED 330 to provide a visual warning signal and/or a horn 335 to provide an audio warning signal. For example, a warning signal may be provided in response to the counting signal having a duty cycle of 51%, which may correspond to a detecting signal with a duty cycle of 15%.

As discussed, the present invention compensates for changing inductance due to changing fluid temperature. Because the inductance values of both coils 118,120 both change in response to temperature, and the inductance values of each coil are indirectly compared to each other, the present invention is able to distinguish between the changing inductance value due to temperature and those inductance values that are attributed to particle accumulation.

Figure 4:
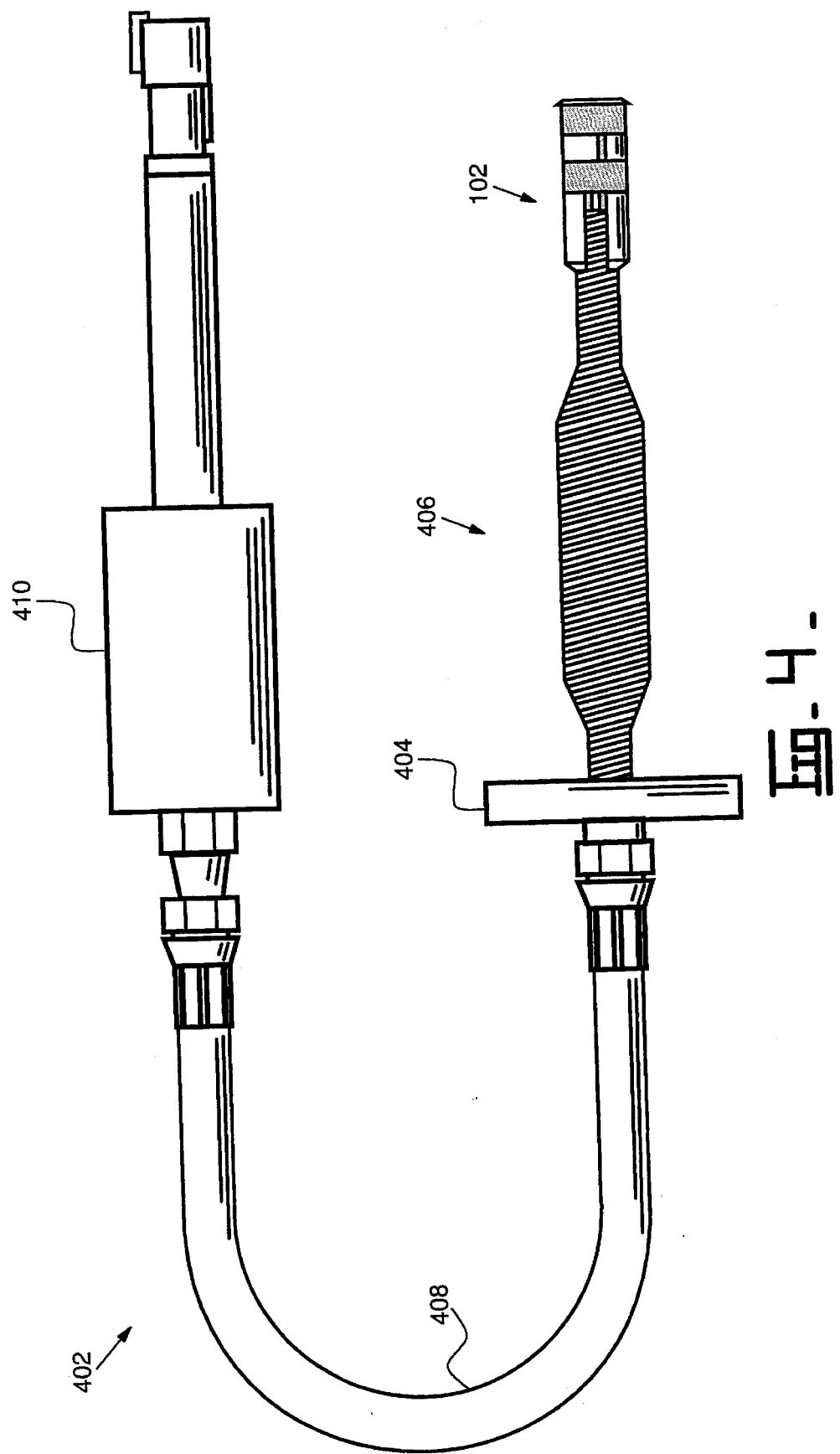
FIG. 4 is an illustration of a flexible dipstick assembly associated with the particle detecting apparatus.

In some applications, placement of the particle sensor 102 in a suitable position is adversely affected by the fluid container, for example, a final drive cavity. One solution to this problem is a dipstick assembly 402, as shown in FIG. 4. The dipstick assembly 402 includes a dipstick cap 404, a flexible dipstick 406, and a flexible joint 408. The flexible joint 408 carries electrical wiring that connects the coils 118,120 to the electrical circuitry that is mounted on a circuit board in box 410. A piece of hydraulic hose has been found to be suitable material for the flexible joint 408. The particle sensor 102 is connected at the end of the flexible dipstick 406, as shown. The flexible dipstick 406 is constructed of wound wire or "steel auger". The steel auger has the advantage of axial strength and flexibility.

Figure 5:
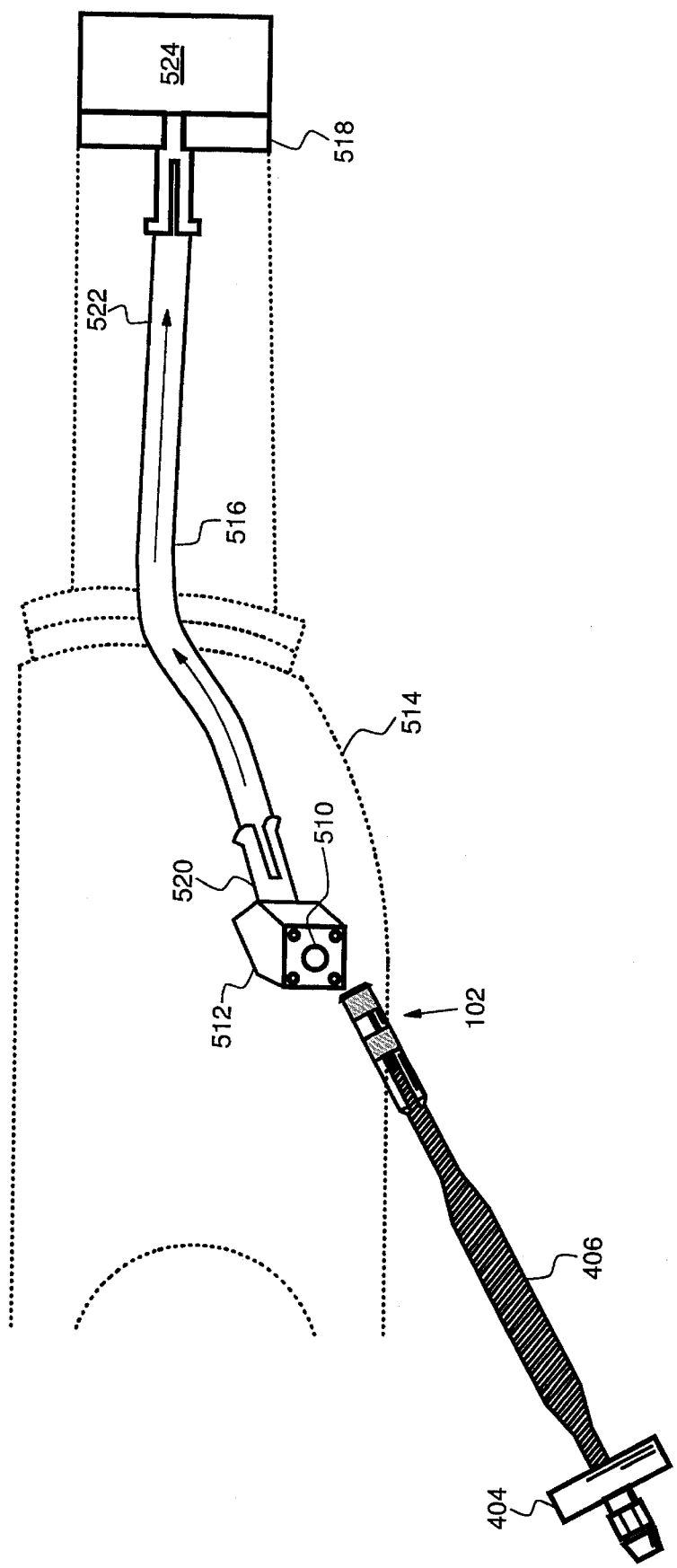
FIG. 5 is an illustration of the flexible dipstick assembly as applied to a differential housing.

One advantage of this arrangement is that the dipstick assembly 402 can be inserted through the oil fill access hole 510 of a differential housing 514, shown in FIG. 5. An access port manifold 512 is mounted to the differential housing 514 (shown in dotted lines). The dipstick assembly 402 is inserted into the access port manifold 512 and passes through a tube 516. The tube 516 is connected to the access port manifold and to a reaction plate 518 via first and second clamps 520,522. The dipstick assembly 402 is inserted such that the particle sensor 102 passes through the second hose clamp 522 and is in position to collect particles from the final drive cavity 524.

The dipstick arrangement also allows the sensor 102 to be inspected without disassembly of the final drive.

Thus, while the present invention has been particularly shown and described with reference to the preferred embodiment above, it will be understood by those skilled in the art that various additional embodiments may be contemplated without departing from the spirit and scope of the present invention.

INDUSTRIAL APPLICABILITY

With reference to the drawings and in operation, the present invention or sensor 102 is adapted to detect metal particles within a fluid. The sensor 102 is particularly well suited to detect metal particles within the lubricating fluid within the system components on a vehicle, for example, within the vehicle's transmission, engine oil pan or final drive. The sensor 102 is designed such that metal particles are attracted by the magnet 116, which settle into the cavity 106. The oscillating circuit energizes the first and second coils 118,120 with an oscillating waveform. The frequency of the oscillating waveform is directly related to the inductance of the coils 118,120. The second coil 120 is utilized to compensate for the inductance changes in response to the fluid temperature.

The metal particles trapped within the cavity 106 affect the inductance of the first coil 118 such that the frequency of the oscillating waveform is indicative of the particles within the cavity 106. The output signal is received by the electronic monitoring system 325 which utilizes the information contained within the output signal to perform its functions. For example, the electronic monitoring system may be adapted to generate a visual operator signal indicative of the amount or size of particles contained within the cavity.

In the preferred embodiment, the plastic housing 104 is an integral one-piece unit which contains the magnet 116, the first and second coils 118,120, the screen 110, and the cavity 106.

In some applications, for example, the final drive mentioned above, the sensor 102 is attached to a long "dipstick" or flexible member that slides through a fixed tube. The dipstick arrangement allows the sensor 102 to be placed and removed from within the final drive. Because the sensor can be easily removed, cleaning and checking of the sensor can be easily accomplished.

Other aspects, objects and advantages of the present invention can be obtained from a study of the drawings, the disclosure and the appended claims.

We claim:

1. An apparatus for detecting particles within a fluid, comprising:

a housing defining a cavity having a bottom surface;

a magnet disposed adjacent the bottom surface of the cavity and adapted to attract and contain particles within the cavity;

a first coil wound in a helix about the outer surface of the cavity, wherein the induction of the first coil is responsive to the particle accumulation within the cavity; and a second coil wound in a helix about the magnet, wherein the induction of the second coil is responsive to the temperature of the fluid and independent to the particle accumulation within the cavity.

2. An apparatus, as set forth in claim 1, including a screen adapted to divide the cavity into an upper portion and a lower portion, the screen adapted to pass smaller particles to the lower portion while retaining larger particles in the upper portion, wherein the inductance of the first coil is responsive to the accumulation of the larger particles and independent to the accumulation of the smaller particles.

3. An apparatus, as set forth in claim 2, wherein the housing is formed from molded plastic to form an integral unit.

4. An apparatus, as set forth in claim 3, including an oscillator adapted to energize the first and second coils.

5. An apparatus, as set forth in claim 4, including a multiplexer adapted to variously select one coil to be energized at a time.

6. An apparatus, as set forth in claim 5, wherein the one energized coil produces an oscillating waveform having a series of pulses, the waveform frequency being a function of the coil inductance.

7. An apparatus, as set forth in claim 6, including a counter adapted to tally the number of waveform pulses associated with the one energized coil, the counter resetting in response to tallying a predetermined number of pulses, responsively the multiplexer selecting the other coil to be energized, wherein the counter tallies the number of waveform pulses associated with the other energized coil.

8. An apparatus, as set forth in claim 7, wherein the counter produces a counting signal having a pulse width modulated waveform, the "high" pulse duration of the counting signal is responsive to the waveform frequency associated with the one coil and the "low" pulse duration is responsive to the waveform frequency associated with the other coil.

9. An apparatus, as set forth in claim 8, including a microprocessor adapted to receive the counting signal, amplify the duty cycle of the counting signal, and responsively produce a detecting signal having a pulse width modulated waveform.

10. An apparatus, as set forth in claim 9, including an electronic monitoring system adapted to receive the detecting signal and produce a warning signal in response to the detecting signal duty cycle being greater than a predetermined value.

11. Am apparatus, as set forth in claim 3, including a dipstick assembly, comprising:

an extending flexible dipstick portion, the housing being connected at an end of the dipstick portion;

a flexible joint that carries electrical wiring to the coils from externally mounted electrical circuitry; and a dipstick cap that separates the flexible joint and the flexible dipstick portion, the dipstick cap being used to mount the dipstick portion.

12. An apparatus for detecting particles within a fluid, comprising:

a housing defining a cavity having a bottom surface;

a magnet disposed adjacent the bottom surface of the cavity and adapted to attract and contain particles within the cavity;

a first coil wound in a helix about the outer surface of the cavity, wherein the induction of the first coil is responsive to the particle accumulation within the cavity; a second coil wound in a helix about the magnet, wherein the induction of the second coil is responsive to the temperature of the fluid and independent to the particle accumulation within the cavity; and a nonmagnetic screen adapted to divide the cavity into an upper portion and a lower portion, the screen adapted to pass smaller particles to the lower portion while retaining larger particles in the upper portion.

13. An apparatus, as set forth in claim 11, wherein the inductance of the first coil is responsive to the accumulation of the larger particles in the upper portion of the cavity and independent to the accumulation of the smaller particles in the lower portion of the cavity.

14. An apparatus, as set forth in claim 13, wherein the housing is formed from molded plastic to form an integral unit.

15. An apparatus for detecting particles within a fluid, comprising:

a housing defining a cavity having a bottom surface;

a magnet disposed adjacent the bottom surface of the cavity and adapted to attract and contain particles within the cavity;

a first coil wound in a helix about the outer surface of the cavity, wherein the induction of the first coil is responsive to the particle accumulation within the cavity;

a second coil wound in a helix about the magnet, wherein the induction of the second coil is responsive to the temperature of the fluid and independent to the particle accumulation within the cavity; and means for variously energizing one coil at a time.

16. An apparatus, as set forth in claim 15, wherein the energizing means includes:

an oscillator adapted to energize the first and second coils; and a multiplexer adapted to variously select one coil to be energized at a time.

17. An apparatus, as set forth in claim 16, wherein the one energized coil produces an oscillating waveform having a series of pulses, the waveform frequency being a function of the coil inductance.

18. An apparatus, as set forth in claim 17, including a counter adapted to tally the number of waveform pulses associated with the one energized coil, the counter resetting in response to tallying a predetermined number of pulses, thereafter the multiplexer selecting the other coil to be energized, wherein the counter tallies the number of waveform pulses associated with the other energized coil.

19. An apparatus, as set forth in claim 18, wherein the counter produces a counting signal having a pulse width modulated waveform, the "high" pulse duration of the counting signal is responsive to the waveform frequency associated with the one coil and the "low" pulse duration is responsive to the waveform frequency associated with the other coil.

20. An apparatus, as set forth in claim 21, including a microprocessor adapted to receive the counting signal, amplify the duty cycle of the counting signal, and responsively produce a detecting signal having a pulse width modulated waveform.

21. An apparatus, as set forth in claim 20, including an electronic monitoring system adapted to receive the detecting signal and produce a warning signal in response to the detecting signal duty cycle being greater than a predetermined value.

* * * * *